United States Patent
Olson (10) Patent No.: US 10,870,110 B2
(45) Date of Patent: Dec. 22, 2020

(54) SPECIMEN CONTAINER AND CENTRIFUGATION METHOD FOR SEPARATING SERUM OR PLASMA FROM WHOLE BLOOD THEREWITH

(71) Applicant: Babson Diagnostics, Inc., Austin, TX (US)

(72) Inventor: Eric Olson, North Salem, NY (US)

(73) Assignee: Babson Diagnostics, Inc., Austin, TX (US)

( * ) Notice: Subject to any disclaimer, the term of this patent is extended or adjusted under 35 U.S.C. 154(b) by 196 days.

(21) Appl. No.: 16/061,309

(22) PCT Filed: Dec. 12, 2016

(86) PCT No.: PCT/US2016/066236
§ 371 (c)(1),
(2) Date: Jun. 11, 2018

(87) PCT Pub. No.: WO2017/100798
PCT Pub. Date: Jun. 15, 2017

(65) Prior Publication Data
US 2018/0353952 A1 Dec. 13, 2018

Related U.S. Application Data (60) Provisional application No. 62/266,433, filed on Dec. 11, 2015.

(51) Int. Cl.
*G01N 21/07* (2006.01)
*B01D 21/26* (2006.01)
(Continued)

(52) U.S. Cl.
CPC .......... *B01L 3/50215* (2013.01); *B01D 21/26* (2013.01); *G01N 21/07* (2013.01);
(Continued)

(58) Field of Classification Search
CPC .... B01L 3/50215; B01L 3/14; A61B 5/15003; A61B 5/154; A61B 5/15; A61B 5/150351; B01D 21/26; G01N 21/07
(Continued)

(56) References Cited

U.S. PATENT DOCUMENTS 2,110,237 A * 3/1938 Parsons .................. G01N 33/04
73/61.71
2,240,101 A * 4/1941 Smith .................. B01L 3/50825
422/550

(Continued)

FOREIGN PATENT DOCUMENTS

CN 103308376 A 9/2013
JP 2000-084389 A 3/2000
(Continued)

OTHER PUBLICATIONS

PCT Written Opinion and Search Report for International Application No. PCT/US2016/066236, dated Mar. 3, 2017.

*Primary Examiner* — Arlen Soderquist (57) ABSTRACT

A device and method for separating serum or plasma from blood cells in a whole blood specimen. The present invention uses a cap with a reservoir, such that blood cells are packed into the cap when the specimen container is centrifuged. When the cap is removed, the blood cells are also removed, and the serum or plasma is left in the specimen tube where it can be readily extracted by a pipette which is able to reach all the way to the bottom of the specimen tube minimizing the dead volume.

30 Claims, 5 Drawing Sheets

(51) Int. Cl.
    *B01L 3/00*         (2006.01)
    *A61B 5/15*        (2006.01)
    *A61B 5/154*      (2006.01)

(52) U.S. Cl.
CPC .......... *A61B 5/15003* (2013.01); *A61B 5/154* (2013.01); *B01L 2300/042* (2013.01); *B01L 2300/044* (2013.01); *B01L 2300/047* (2013.01); *B01L 2300/0832* (2013.01)

(58) Field of Classification Search
USPC ........... 422/72–73, 533–534, 547–550, 568; 436/45, 69–70, 165, 177, 810; 494/19–20, 43, 57, 36–37
See application file for complete search history.

(56) References Cited

U.S. PATENT DOCUMENTS

| | | | | |
|---|---|---|---|---|
| 2,775,350 | A * | 12/1956 | Jones | B01D 35/02 210/446 |
| 3,081,029 | A * | 3/1963 | Gauslaa | B01L 3/5021 494/38 |
| 3,300,051 | A * | 1/1967 | Mitchell | B01L 3/569 210/339 |
| 3,326,400 | A * | 6/1967 | Hamelin | B65D 51/2871 206/221 |
| 3,419,179 | A * | 12/1968 | Deuschle | B01L 3/5082 220/375 |
| 3,434,859 | A * | 3/1969 | Benjamin | A61B 10/00 427/476 |
| 3,478,889 | A * | 11/1969 | Fessler | B01L 3/5635 210/406 |
| 3,481,712 | A * | 12/1969 | Bernstein | B04B 5/0414 422/548 |
| 3,508,653 | A * | 4/1970 | Coleman | G01N 33/491 210/789 |
| 3,525,254 | A * | 8/1970 | Milanes | G01N 33/86 73/64.41 |
| 3,539,300 | A * | 11/1970 | Stone | A61B 5/15003 422/73 |
| 3,615,222 | A * | 10/1971 | Mead | B01L 3/5082 436/500 |
| 3,684,455 | A * | 8/1972 | Vacirca | B01L 3/5082 422/413 |
| 3,701,434 | A * | 10/1972 | Moore | B01D 35/00 210/477 |
| 3,706,305 | A * | 12/1972 | Berger | A61B 5/15003 600/575 |
| 3,706,306 | A * | 12/1972 | Berger | A61B 5/15003 600/575 |
| 3,733,179 | A * | 5/1973 | Guehler | B01L 3/502 436/71 |
| 3,761,408 | A * | 9/1973 | Lee | A61B 5/154 210/782 |
| 3,768,979 | A * | 10/1973 | Mead | G01N 33/487 422/430 |
| 3,818,188 | A | 6/1974 | Hertel et al. | |
| 3,852,194 | A * | 12/1974 | Zine, Jr. | G01N 33/491 210/789 |
| 3,928,139 | A * | 12/1975 | Dorn | C12Q 1/24 435/34 |
| 3,938,953 | A * | 2/1976 | Paschalis | G01N 33/78 436/500 |
| 3,939,822 | A * | 2/1976 | Markowitz | A61B 5/15003 600/575 |
| 3,942,717 | A * | 3/1976 | Robison | B01L 3/5021 494/43 |
| 3,958,944 | A * | 5/1976 | Wong | B01L 3/5082 422/72 |
| 4,012,325 | A * | 3/1977 | Columbus | B01L 3/5021 210/516 |
| 4,050,451 | A * | 9/1977 | Columbus | A61B 5/15003 600/577 |
| 4,052,320 | A * | 10/1977 | Jakubowicz | B01L 3/0272 210/516 |
| 4,081,356 | A * | 3/1978 | Zierdt | A61B 10/0038 209/17 |
| 4,136,036 | A * | 1/1979 | Columbus | A61B 5/150022 210/516 |
| 4,154,690 | A * | 5/1979 | Ballies | B01L 3/50215 210/516 |
| 4,169,060 | A * | 9/1979 | Columbus | A61B 5/15003 210/516 |
| 4,227,620 | A * | 10/1980 | Conway | B01L 3/5082 215/355 |
| 4,294,707 | A * | 10/1981 | Ikeda | B01L 3/50215 210/359 |
| 4,308,232 | A * | 12/1981 | Crouther | A61L 33/0017 422/550 |
| 4,443,408 | A | 4/1984 | Mintz | |
| 4,591,486 | A * | 5/1986 | Eberle | G01N 1/2813 422/72 |
| 4,671,939 | A * | 6/1987 | Mintz | G01N 33/86 356/246 |
| 4,832,678 | A * | 5/1989 | Sheeran | B04B 5/0414 422/552 |
| 5,275,731 | A * | 1/1994 | Jahn | G01N 33/491 210/515 |
| 5,501,841 | A | 5/1996 | Lee et al. | |
| 5,882,318 | A * | 3/1999 | Boyde | A61B 5/15003 600/595 |
| 5,882,943 | A * | 3/1999 | Aldeen | B01L 3/502 210/323.2 |
| 5,975,313 | A | 11/1999 | Sarstedt | |
| 6,132,353 | A | 10/2000 | Winkelman et al. | |
| 6,270,728 | B1 | 8/2001 | Wijnschenk et al. | |
| 7,176,034 | B2 * | 2/2007 | Efthimiadis | A61B 10/0051 422/534 |
| 8,343,426 | B2 * | 1/2013 | Song | B01L 3/5021 210/645 |
| 8,550,273 | B2 * | 10/2013 | Levin | B01L 3/5082 215/321 |
| 9,279,760 | B2 | 3/2016 | Imazu et al. | |
| 2004/0005246 | A1 * | 1/2004 | Efthimiadis | A61B 10/0051 422/534 |
| 2004/0059255 | A1 * | 3/2004 | Manoussakis | B01L 3/5021 600/573 |
| 2004/0129631 | A1 * | 7/2004 | Anraku | B01L 3/50215 210/500.1 |
| 2005/0014273 | A1 | 1/2005 | Dahm et al. | |
| 2005/0059163 | A1 | 3/2005 | Dastane et al. | |
| 2005/0123444 | A1 | 6/2005 | Tomasso et al. | |
| 2007/0020629 | A1 | 1/2007 | Ross et al. | |
| 2007/0073187 | A1 | 3/2007 | Thomson et al. | |
| 2007/0083131 | A1 | 4/2007 | Escutia et al. | |
| 2008/0213377 | A1 | 9/2008 | Bhatia et al. | |
| 2008/0313877 | A1 | 12/2008 | Campbell | |
| 2010/0261988 | A1 | 10/2010 | Tamir | |
| 2012/0048002 | A1 | 3/2012 | Mallet | |
| 2012/0048827 | A1 * | 3/2012 | Levin | B01L 3/5082 215/329 |
| 2012/0058027 | A1 * | 3/2012 | Song | B01L 3/5021 422/533 |
| 2014/0065018 | A1 | 3/2014 | Imazu et al. | |
| 2014/0241957 | A1 | 8/2014 | Serhan et al. | |
| 2014/0255254 | A1 | 9/2014 | Yamaguchi et al. | |
| 2014/0273242 | A1 | 9/2014 | Ochranek et al. | |
| 2014/0296089 | A1 | 10/2014 | Holmes et al. | |
| 2014/0374480 | A1 | 12/2014 | Pollack | |
| 2015/0289856 | A1 * | 10/2015 | Saqi | B01L 3/502 422/534 |
| 2015/0316532 | A1 | 11/2015 | Makino et al. | |

FOREIGN PATENT DOCUMENTS

| | | |
|---|---|---|
| JP | 2014-048112 A | 3/2014 |
| JP | 2014-173904 A | 9/2014 |
| WO | 2013003308 A1 | 1/2013 |
| WO | 2014050021 A1 | 9/2013 |
| WO | WO 2017/100798 A1 | 6/2017 |

(56) References Cited

FOREIGN PATENT DOCUMENTS

| WO | WO 2018/090023 A1 | 5/2018 |
| WO | WO 2018/090027 A1 | 5/2018 |
| WO | WO 2018/090030 A2 | 5/2018 |

* cited by examiner

SPECIMEN CONTAINER AND CENTRIFUGATION METHOD FOR SEPARATING SERUM OR PLASMA FROM WHOLE BLOOD THEREWITH

CROSS-REFERENCE TO RELATED APPLICATIONS

This application is a U.S. National Phase application, filed under U.S.C. § 371(c), of International Application No. PCT/US2016/066236, filed Dec. 12, 2016, which claims priority of U.S. Provisional Appl. No. 62/266,433, filed Dec. 11, 2015, both of which are incorporated by reference herein in their entireties.

TECHNICAL FIELD

The present invention relates to a device and method for separating serum or plasma from whole blood.

BACKGROUND

Many in vitro diagnostic testing systems and protocols require the use of blood specimens that are free of blood cells in order to perform a diagnostic test. These diagnostic tests either use serum or plasma which is separated from whole blood using techniques such as centrifugation or filtration.

Serum can be separated from whole blood by first allowing the blood to clot and then centrifuging the specimen to move all the blood cells to the bottom of the specimen tube. Plasma can be separated from whole blood by first mixing the whole blood with an anticoagulant such as lithium heparin or potassium EDTA and then centrifuging the specimen to move all the blood cells to the bottom of the specimen tube.

When using centrifugation to separate serum or plasma from whole blood, it is common to use a specimen tube that contains a thixotropic gel which has a greater specific gravity than serum or plasma, but lower specific gravity than blood cells. During centrifugation, this gel migrates above the blood cells while staying below the serum or plasma. The function of the gel is to provide a barrier between the serum or plasma and the blood cells so that the serum or plasma do not remix with the blood cells after centrifugation.

One difficulty of using serum or plasma from centrifuged specimen tubes is that it is difficult to extract serum or plasma from the specimen tube without leaving a large dead volume. The term "dead volume" refers to the amount of unusable sample left in the specimen tube after the maximum amount of sample has been extracted. When using an automated or manual pipette to extract sample from a centrifuged specimen tube, there is a risk that the pipette will make contact with either the blood cells or the gel separator. If this occurs, the sample may be disturbed remixing the blood cells and serum or plasma, the pipette may get clogged, or the pipette may not extract pure serum or plasma. To avoid these risks, the pipette must be kept a safe depth above the blood cells or gel separator to ensure it does not make contact with the blood cells or the gel separator. For an automated pipette, this means that the pipette depth is controlled such that the pipette tip keeps a safe distance from the blood cells or the gel separator. For a manual pipette, this means that the user exercises caution to keep the pipette a safe distance from the blood cells or the gel separator. The serum or plasma which is above the blood cells or the gel separator yet below the pipette tip is unusable as it won't be extracted in the pipette.

Leaving a large dead volume may not be problematic when the amount of serum or plasma available is significantly greater than the amount required by the diagnostic tests. However, as the amount of serum or plasma required by the diagnostic tests approaches the amount of serum or plasma available, dead volume becomes a greater concern. This is particularly important when using small volume sample collection technologies or in pediatric samples where the amount of blood able to be drawn is more limited.

In cases where it is not possible to collect larger amounts of a blood specimen, one common technique to reduce the dead volume left when pipetting from a centrifuged specimen container is to pour the serum or plasma out of the centrifuged specimen tube, into a secondary specimen tube. Because the secondary specimen tube does not contain blood cells or gel separator, a pipette can safely dive to the bottom of the specimen tube and the serum or plasma can be extracted with a low dead volume. While this technique results in a low dead volume, there are several significant disadvantages. This technique consumes an additional specimen container, which results in added material costs. The step of pouring serum or plasma increases labor costs and introduces risk of human error. There is also a risk of specimen mix-up if the new specimen tube is not properly labeled.

In order to, inter alia, make a blood draw less invasive and decrease the costs of the running diagnostic tests, many companies are currently developing specimen collection and processing techniques based on smaller sample volumes than are collected by most labs today. In order to effectively run diagnostic tests using serum or plasma collected in small volumes, approaches are needed to minimize the loss of serum or plasma due to dead volume. This invention enables diagnostic laboratories to effectively run diagnostic tests using smaller blood specimens or run more tests with the same volume of blood specimen.

SUMMARY

Provided herein is a device for separating serum or plasma from blood cells in a whole blood specimen. The present invention uses a cap with a reservoir, such that blood cells are packed into the cap when a specimen tube is centrifuged with the capped end away from the axis of centrifugation. When the cap is removed, the blood cells are also removed, so that the serum or plasma is left in the specimen tube where it can be readily extracted by a pipette which is able to reach all the way to the bottom of the specimen tube minimizing the dead volume.

DETAILED DESCRIPTION OF ILLUSTRATIVE EMBODIMENTS

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise.

The term "about" as used herein when referring to a measurable value such as an amount and the like, is meant to encompass variations of up to ±30% from the specified value, as such variations are appropriate to perform the disclosed methods. Unless otherwise indicated, all numbers expressing quantities of properties such as volume and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Figure 1A:
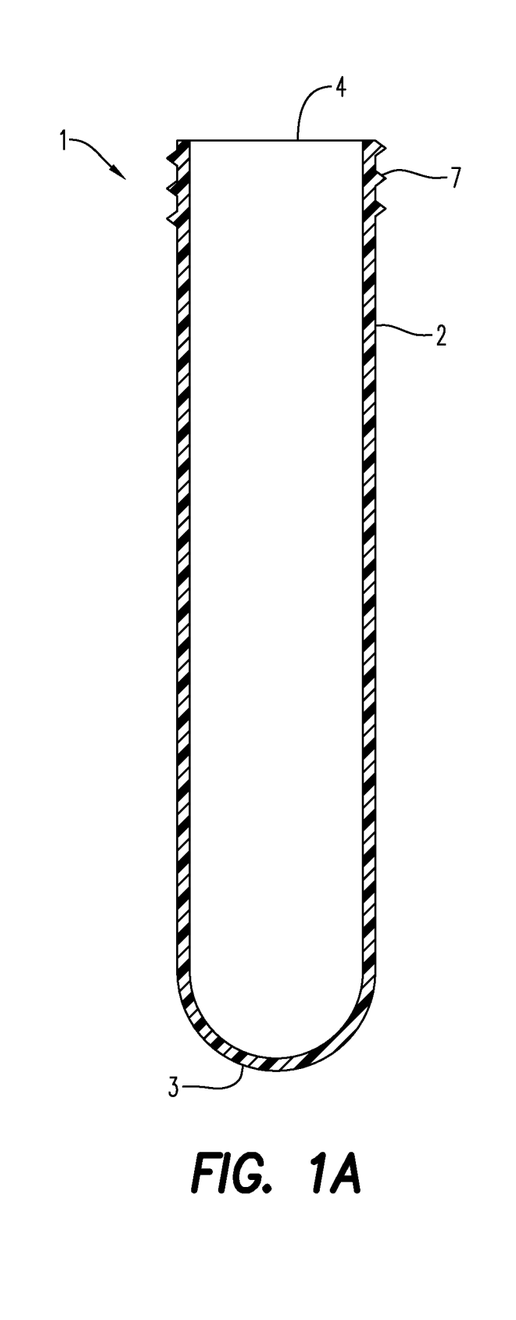
FIGS. 1A and 1B shows a cross-sectional view of the specimen tube and cap according to the invention.

FIG. 1 depicts a specimen tube, often called a test tube, in which a blood specimen is collected according to the present invention. The specimen tube 1 has a closed end 3, open end 4 and lateral wall(s) 2. The open end 4 enables a liquid specimen to be inserted into the specimen tube 1. The closed end 3 is shown in a preferred embodiment with a round bottom. Specimen tubes having a round or conical bottom are preferred as they minimize dead volume when pipetting from the bottom of the specimen tube. While specimen tubes with round or conical bottoms are preferred, the bottom of the specimen tube can be any shape.

Figure 1B:
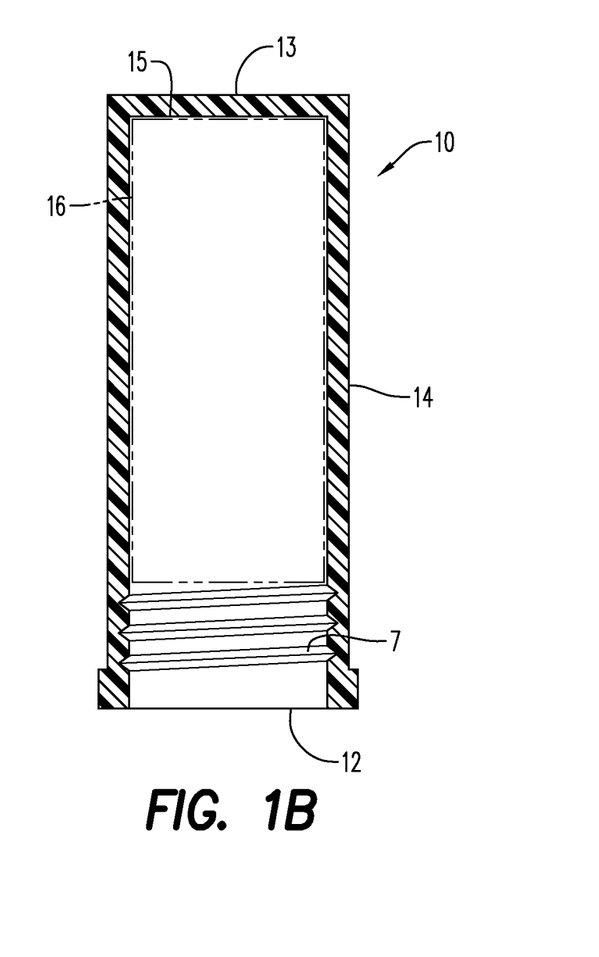
Figure 2:
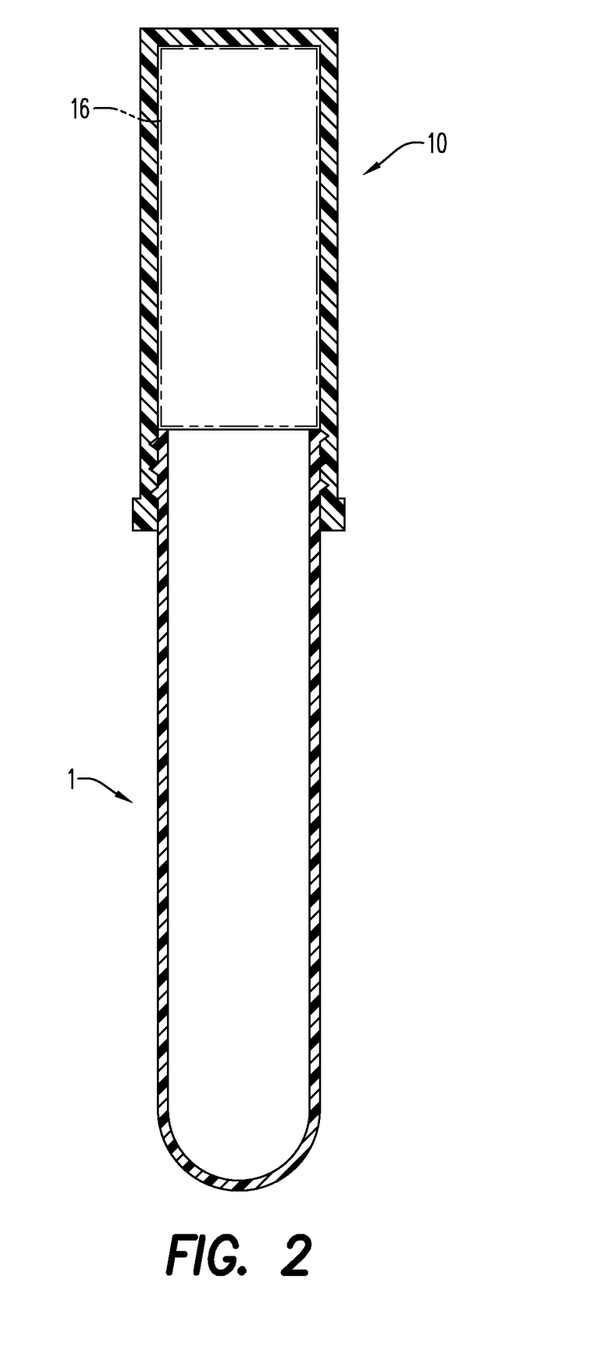
FIG. 2 shows a cross-sectional view of the specimen container according to the invention.

FIG. 1B depicts a cap 10 to secure onto a specimen tube such as that shown in FIG. 1A. The cap 10 has an open end 12, a closed end 13 and a lateral wall 14. The closed end 13 is closed by a surface 15. The cap 10 has a reservoir 16 which is formed when the cap 10 and specimen tube 1 are secured to formed a specimen container comprising the specimen tube and the cap, as shown in FIG. 2, where the volume of the reservoir 16 is defined as the maximum amount of liquid that can be contained in the cap 10 without coming into contact with the specimen tube 1. In order to remove the blood cells or other solids in the blood from the serum or plasma in accordance with the present invention, the volume of the reservoir 16 should be equal to or greater than the volume of the blood cells and other solids to be separated from the serum or plasma in the blood specimen. This will enable to the blood cells and other solids to be removed when the cap 10 is removed from the specimen tube 1. In another embodiment, the cap is sized so that volume of the reservoir is equal to or greater than the volume of whole blood in the specimen tube. This design will decrease or eliminate the pressure on the seal between the specimen tube and the cap during centrifugation.

The specimen tube 1 and cap 10 have a mechanism by which the open end 4 of the specimen tube 1 may be secured with the open end 12 of the cap 10 to form a specimen container, such that the blood specimen is contained within the specimen tube 1 and the cap 10. The mechanism for securing the specimen tube 1 and the cap 10 can be any mechanism desired as long as the specimen tube and cap are secured to create a leak free fitting. It is important that the contents of the specimen container do not leak when the specimen container is oriented in any direction. Such mechanisms for securing the specimen tube to the cap can include an engineered fit or interference fit. A preferred engineered fit is a threaded connection 7 where the specimen tube and the cap both have screw threads that work to connect the specimen tube and the cap together as shown in the figures. Any other engineered fit can be used that creates a leak free locking mechanism. Alternatively, an interference fit can be used such that the specimen tube and the cap are secured by friction after the open end of the specimen tube and open end of the cap are pushed together. For example, the cap can be a plug that is secured onto the open end of the specimen tube. Optionally, the joint between the specimen tube and the cap can be sealed using a gasket. The mechanism to secure the specimen tube and cap together is not limited to any particular mechanism and shall include any mechanism whereby the specimen tube and cap can be secured together to create a leak free specimen container.

Figure 3A:
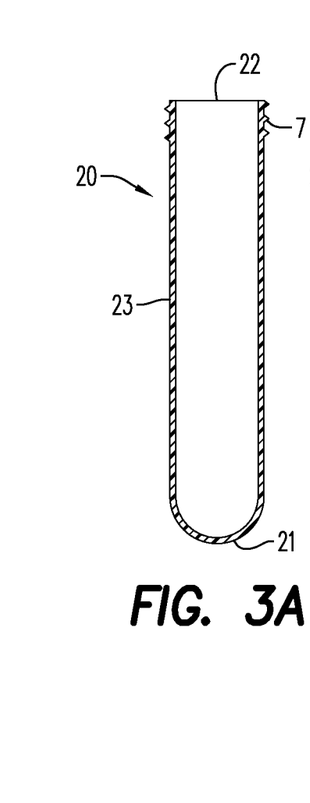
FIG. 3A-3I depicts the methodology for separating serum or plasma from blood cells according to the invention.
Figure 3B:
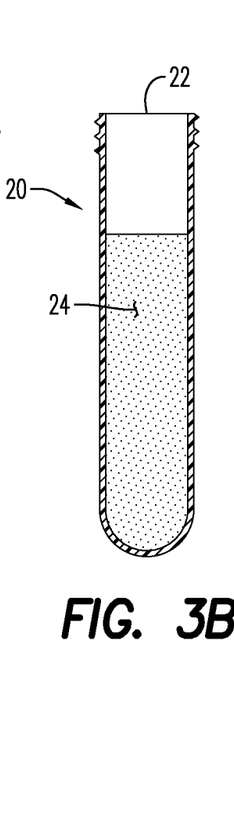
Figures 3C, 3D:
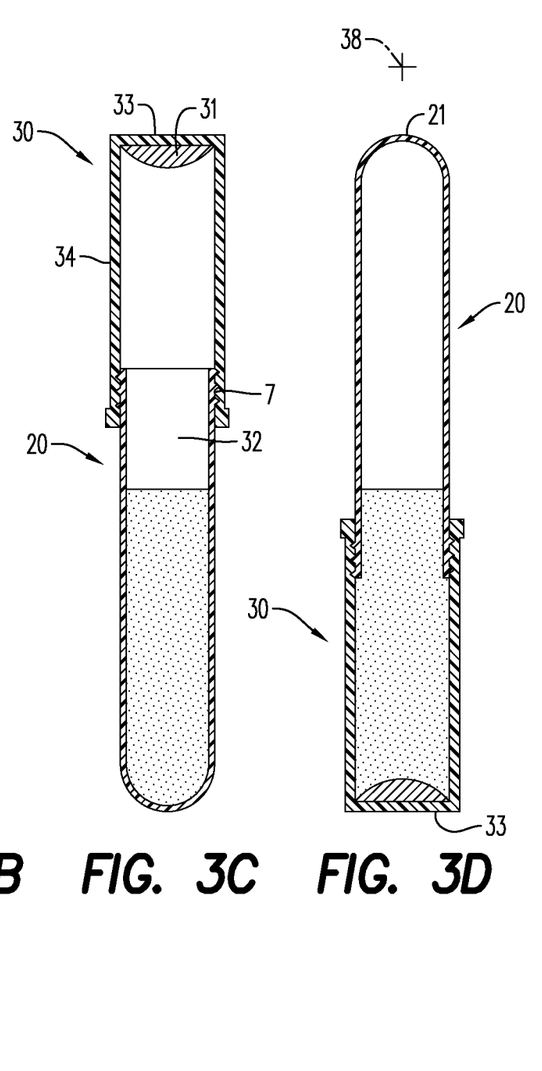

FIGS. 3A-3I depict an embodiment of the inventive method to separate serum or plasma from a blood specimen and works as follows:

In FIG. 3A an empty specimen tube 20 having a closed end 21, open end 22 and lateral wall(s) 23 is shown. FIG. 3B shows the specimen tube 20 filled with a whole blood specimen 24 which was inserted through open end 22. In FIG. 3C, a cap 30, such as that shown in FIG. 1B, is secured to the open end 22 of the specimen tube 20. A specimen tube that is enclosed with a cap is referred to herein as a specimen container. The cap has an open end 32, a closed end 33 and a lateral wall 34. The cap 30 contains a separator 31.

For purposes of this invention, a separator is a device that is put into a specimen tube (or alternatively, into a cap) in order to ensure that after the specimen tube is centrifuged, there is a physical layer separating the serum or plasma from the blood cells and other solids. The separator is chosen such that it has a higher specific gravity than serum and/or plasma and lower specific gravity than blood cells and other solids in the blood to be removed. During centrifugation, the serum or plasma is separated from blood cells and any other solids in the blood by migrating closer to the axis of centrifugation because it has lower specific gravity. The blood cells (and other solids) migrate further away from the axis of centrifugation because they have higher specific gravity. The separator migrates to a level between the serum or plasma and the blood cells (and other solids), because it has intermediate specific gravity. The primary function of the separator is to maintain the purity of the serum or plasma by 1) preventing the serum or plasma from remixing with the blood cells, and 2) preventing the serum or plasma from becoming contaminated by the blood cells as they degrade.

A preferred separator is a thixotropic gel. This is a hydrophobic gel which is initially solid, but becomes liquefied during centrifugation so that it can migrate to form a layer between the serum or plasma and the blood cells (and other solids). A preferred thixotropic gel is a polyester based formulation, however any thixotropic gel can be used. Other nonlimiting examples are a mixture of silicon fluid and a hydrophobic powdered silica or a mixture of a hydrocarbon polymer and a powdered silica. Another preferred embodiment uses a thixotropic gel which is UV-curable in order to improve the strength of the barrier that is formed between the serum or plasma and the blood cells and other solids. Alternative types of separators include mechanical separators (e.g. elastomer barriers such as used in BD Barricor technology) and filter-based separators.

Figure 3E:
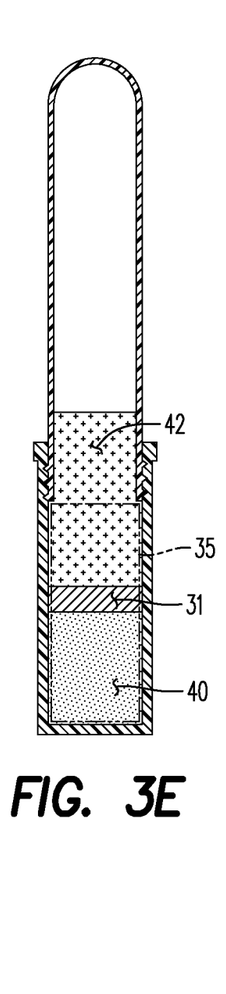
Figures 3F, 3G:
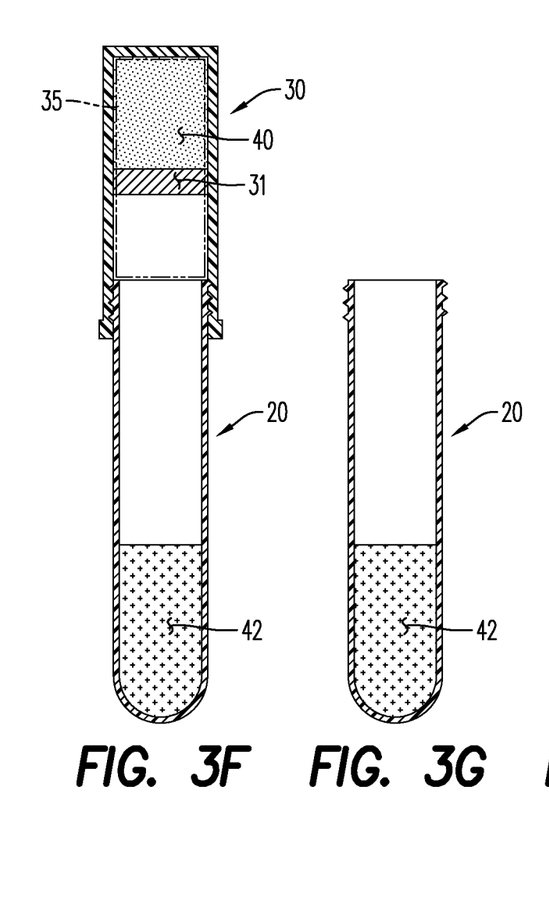
Figure 3H:
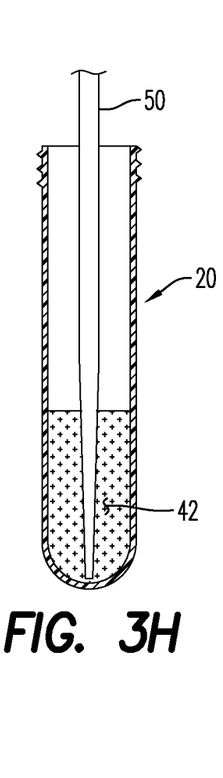
Figure 3I:
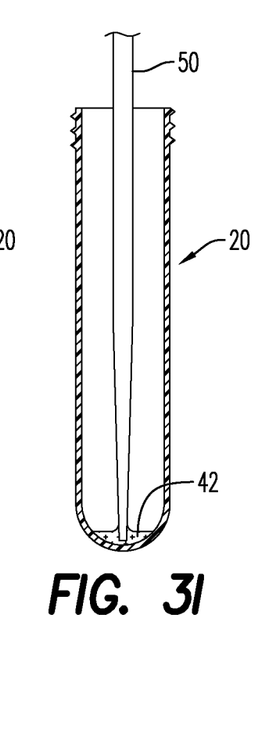

In the preferred embodiment shown in FIG. 3A-3I, the separator 31 is a thixotropic gel. In FIG. 3D, the specimen container is centrifuged while oriented such that the closed end 33 of the cap 30 is further away from the axis of centrifugation 38 than the closed end 21 of the specimen tube 20. During centrifugation, blood cells 40 and any other solids that have a greater specific gravity than serum or plasma migrate to the reservoir 35. FIG. 3E shows the specimen container after it is centrifuged while oriented (in this case shown in an inverted orientation) so that the blood cells 40 migrate toward the closed end 33 of the cap 30 and into the reservoir 35. Due to the difference in specific gravity, the thixotropic gel separator 31 migrates above the blood cells 40 and forms a layer between the serum or plasma 42 and the blood cells 40. The serum or plasma 42 migrates above the thixotropic gel separator 31. In Figure F, the specimen container is orientated upright with the cap 30 above the specimen tube 20 such that gravity moves the serum or plasma 42 to the closed end 21 of the specimen tube 20. The thixotropic gel separator 31 remains in the cap 30 of the specimen container and keeps the blood cells 40 trapped within the cap 30. In FIG. 3G, the cap 30 is removed from the specimen tube 20. The blood cells 40 and thixotropic gel separator 31 are also removed because they are contained within in the reservoir 35. The serum or plasma 42 is retained in the specimen tube 20. In FIG. 3H, a pipette 50 is inserted into the specimen tube 20 to extract the serum or plasma 42. Because there are no blood cells and no separator in the specimen tube, the pipette is able to safely descend to the bottom of the specimen tube to extract the serum or plasma without risk of contacting any of the separator or blood cells. In FIG. 3I, the pipette has extracted nearly all of the serum or plasma, while leaving a very small unusable dead volume. The conventional method of separating serum or plasma from whole blood leaves the blood cells and separator at the bottom of the specimen tube, which results in significantly higher dead volume because the pipette must keep a safe distance from the separator and blood cells to ensure there is no contact. The invention achieves having a significantly smaller dead volume, without incurring the added cost and risk of pouring the serum or plasma into a secondary specimen tube.

An important element of the present invention is the cap design, which includes a reservoir large enough to contain the blood cells from the specimen along with any other solids or separator to be removed. The advantage of containing and capturing blood cells, other solids and any separator within the cap is that when the cap is removed, the blood cells and any other solids or separator are removed with the cap, leaving only serum or plasma in the specimen tube to be pipetted.

Another important element of the present invention is the technique of centrifuging the specimen container while oriented with the closed end of the cap further away from the axis of centrifugation than the closed end of the specimen tube. Centrifuging the specimen container with the closed end of the cap further way from the axis of centrifugation than the closed end of the specimen tube captures the blood cells, other solids and any separator in the reservoir in the cap. This enables the blood cells, other solids and any separator to be removed from the specimen when the cap is removed after centrifugation leaving just the serum or plasma in the specimen tube to be extracted for testing.

Figure 4A:
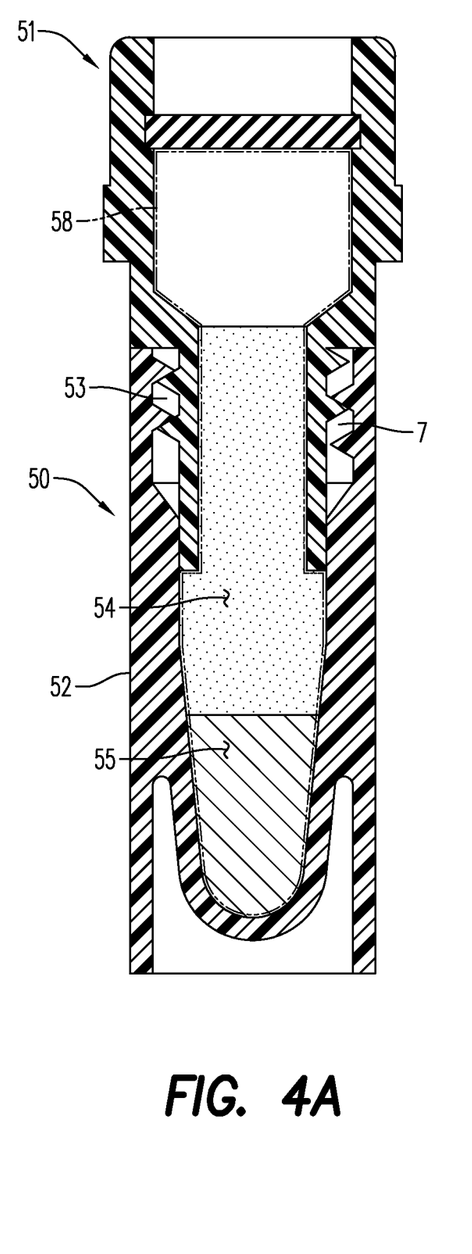
FIGS. 4A and 4B depicts a preferred embodiment of the specimen container according to the present invention.
Figure 4B:
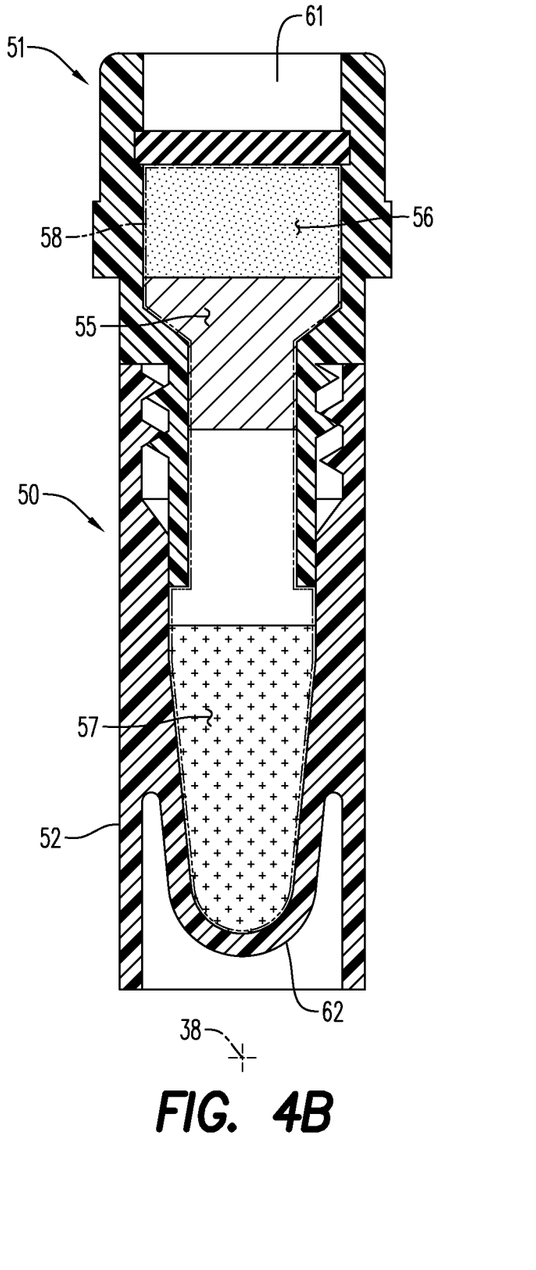

FIGS. 4A and 4B depict a preferred embodiment of the present invention. FIG. 4A depicts a sample container 50 with cap 51 secured to sample tube 52. The cap 51 is secured by threaded connection 53 which secures to the internal threading of the sample tube 52. In this embodiment, the cap 51 is structured such that the reservoir 58 extends into the sample tube 52. The sample container 50 contains a whole blood specimen 54 and a thixotropic gel 55 as a separator. FIG. 4A depicts the sample container prior to centrifugation. FIG. 4B depicts the sample container after centrifugation and shows the blood cells and other solids 56 separated from the serum or plasma 57 by the thixotropic gel 55 which acts as a separator. The sample container was centrifuged with the closed end 61 of the cap 51 further away from the axis of centrifugation 38 than the closed end 62 of the specimen tube 52 so that the components of greater specific gravity (i.e. blood cells and any other solids to be removed from the whole blood specimen) moved to the closed end 61 of the cap 51. The thixotropic gel 55 separator which has a specific gravity intermediate to that of the blood cells and serum or plasma forms a layer between the blood cells and any other solids to be removed and the serum or plasma. The cap 51 can then be removed leaving only serum or plasma contained in the specimen tube.

While particular embodiments of the invention have been described and illustrated, it is not intended that the invention be limited thereto. It is intended that the invention be as broad in scope as the art will allow and that the disclosure herein be interpreted likewise.

FIG. 1A shows a cylindrical specimen tube as is typically used to collect blood specimens, however the specimen tube need not be cylindrical in shape. The invention could apply to specimen tubes with any shape desired.

FIGS. 1A-B, 2, 3A-I, and 4A-B do not show the dimensions of the specimen container. Due to the applicability to small sample volumes, the size of the specimen container is preferably a micro-sample tube in the range of 0.1 mL to 2.0 mL. However, the invention is also applicable to larger conventional specimen tubes in the range of 2.0 mL to 10.0 mL or greater. The invention is not specific to any particular dimension of specimen container and can be applied to specimen tubes of any size.

FIG. 1A shows the use of a specimen tube having a round closed end. This is a preferred embodiment because this geometry minimizes the dead volume for a conventional pipette. The invention is not specific to any particular shape of specimen tube or specimen container and can be applied to specimen tubes or specimen containers of any shape.

FIG. 3B shows whole blood added to the specimen container while there is no cap on the specimen container. An alternate approach would be to add blood to the specimen container while the cap is attached. In this embodiment, the closed end of the cap would contain a pierceable material such that a cannula can be inserted through the closed end of the cap to insert a blood specimen into the specimen container. The pierceable material would need to be such that it will reseal so that the specimen container does not leak the blood specimen contained within. This is commonly done today using evacuated specimen tubes that have a cap with a septum that can be pierced with a needle. In such an embodiment, cap surface 15 in FIG. 1B or at least part thereof would be made up a material capable of being punctured with a needle. The material should be self-sealable such that after it is punctured with a needle, it will reseal so that the specimen does not leak out of the cap.

This embodiment shall also embody any configuration wherein the closed end of the cap can be unsealed and resealed such that a cannula can insert blood through the closed end of the cap.

In another preferred embodiment, the volume inside the specimen container is evacuated. This causes the blood specimen to be pulled into the specimen container by air pressure.

The figures show the specimen container and cap having a screw-type connection in order to connect the cap to the top end of the specimen container. A screw-type connection is the preferred embodiment as it provides the most secure seal for centrifugation. However, the cap may be attached to the specimen container by a variety of methods. A few examples are provided but the invention should not be limited to the examples and should include any method for securing the cap to the specimen container. A stopper-type connection may be used, but extra sealing pressure may be required to be applied during centrifugation. A gasket between the tube and the cap may be useful in such an embodiment to improve the seal.

The preferred embodiment described and illustrated show the specimen tube and cap as standalone components. In another embodiment, the cap may be physically tethered to the specimen container so that they are always connected. Once the blood specimen is centrifuged to separate the serum or plasma from the blood cells and other solids, the cap should be able to be opened such that a pipette is able to be inserted into the specimen tube to pipette the serum or plasma or such that the serum or plasma can be poured out into a separate container such as a different specimen tube.

An alternative embodiment is to integrate the cap into another device. For example, a blood collection device with a threaded opening could act as the cap for a specimen tube. This blood collection device could have a dual function where it puts blood into the specimen tube and also acts as the cap.

An alternative embodiment is to have a single device which functions as multiple caps. For example, a single plastic device with multiple threaded openings could act as the cap for multiple specimen tubes, with each threaded opening having its own reservoir. What is essential is that each threaded opening, which acts as a cap, contains a reservoir large enough to hold the blood cells and any other solids or separator.

An alternative embodiment is to have a single device which functions as multiple specimen tubes. For example, a multi-well plate could act as multiple specimen tubes, with each well in the plate capable of being secured by a cap which contains a reservoir.

The preferred embodiments described and illustrated in FIGS. 3A-3I, 4A and 4B include the use of a thixotropic gel as a separator gel. This design is preferred as the gel provides a reliable barrier to prevent the blood cells from remixing with the serum or plasma. An alternative is to not use any separator and rely on the centrifugation to pack the blood cells tightly enough in the reservoir such that they remain in the cap after centrifugation and when the cap is removed.

FIG. 3C shows the separator (e.g. a thixotropic gel) initially contained in the cap. This embodiment is preferred because it allows the specially designed cap to be used with commodity specimen tubes which do not contain a separator (e.g. a thixotropic gel). An alternative embodiment is to have the separator gel (e.g. a thixotropic gel) initially contained in the specimen tube.

FIG. 3E shows that the size of the reservoir has been designed such that the maximum volume it can hold is the volume of blood cells plus the volume of the separator gel. This minimizes the size of the cap while still ensuring that the blood cells and separator gel will be fully contained within the cap. The cap must be of sufficient size so that the reservoir has a volume sufficient to hold the volume of blood cells plus the volume of any other solids such as the separator. An alternative embodiment is to size the reservoir such that its volume is equal to or greater than the specimen tube's volume. This would ensure that during centrifugation there is no pressure on the seal between the specimen tube and the cap.

The preferred embodiment described and illustrated describe the separation of serum or plasma from whole blood. This implies the possible use of chemical additives to the whole blood. For instance, to separate serum, a clot activator such as silica may be used. To separate plasma, an anticoagulant such as lithium heparin or potassium EDTA can be used. This invention is not limited to the use of any particular additive.

What is claimed:

1. A method of separating serum or plasma from a blood specimen comprising:
    with a specimen tube having an open end, a closed end, a lateral wall extending from the open end to the closed end, and a volume defined therebetween, disposing a blood specimen into the volume through the open end of the specimen tube;
    covering the open end of the specimen tube with a cap, the cap having an open end, a closed end, a lateral wall extending from the open end of the cap to the closed end of the cap, and a reservoir defined therebetween,
    with the cap secured to the specimen tube thereby enclosing the volume and reservoir to collectively form a specimen container therein, and with the blood specimen and a separator disposed within the specimen container, centrifuging the specimen container with the specimen container oriented with the closed end of the cap further away from an axis of centrifugation than the closed end of the specimen tube such that (1) blood cells of the blood specimen having a specific gravity greater than serum or plasma of the blood specimen migrate into the reservoir, and (2) the separator, having a specific gravity greater than the serum or plasma and less than the blood cells, migrates into the reservoir and between the blood cells and serum or plasma; and
    orienting the specimen container so that the closed end of the cap is oriented above the closed end of the specimen tube to enable gravity to move the serum or plasma towards the closed end of the specimen tube while the blood cells and separator remain in the reservoir of the cap, the cap being at least partially removable from the specimen tube to expose the open end of the specimen tube such that the serum or plasma can be withdrawn through the open end of the specimen tube.

2. The method of claim 1, further comprising:
    at least partially removing the cap from the specimen tube to expose the open end of the specimen tube and withdrawing the serum or plasma through the open end of the specimen tube.

3. The method of claim 1, wherein prior to the centrifuging, the cap is secured to the specimen tube such that the cap is spaced apart from the closed end of the specimen tube.

4. The method of claim 1, wherein prior to the centrifuging, the separator is disposed within the volume of the specimen tube.

5. The method of claim 1, wherein the volume of the specimen tube is about 0.1 mL to about 2.0 mL.

6. The method of claim 1, wherein the closed end of the specimen tube is round.

7. The method of claim 1, wherein the closed end of the specimen tube is conical.

8. The method of claim 1, wherein disposing the blood specimen into the volume through the open end of the specimen tube includes inserting the blood specimen into the volume of the specimen tube while the cap is still physically coupled to the specimen tube.

9. The method of claim 1, wherein the reservoir has a volume that is equal to or greater than the volume of the specimen tube.

10. The method of claim 1, wherein the specimen tube is tapered towards its closed end.

11. The method of claim 1, wherein the cap is disposed entirely outside the volume of the specimen tube when the cap is secured to the specimen tube.

12. The method of claim 1, wherein the lateral wall is continuous from the closed end of the specimen tube to the open end of the specimen tube.

13. The method of claim 1, wherein the covering the open end of the specimen tube includes circumferentially surrounding a portion of the specimen tube with a portion of the cap.

14. The method of claim 1, wherein the separator is a thixotropic gel.

15. The method of claim 1, wherein the separator is a mechanical separator.

16. The method of claim 1, wherein the separator is a filter-based separator.

17. The method of claim 1, wherein prior to centrifuging, the separator is in solid form, the centrifuging including liquefying the separator so that the separator can migrate within the specimen container and form a layer between the serum or plasma and the blood cells.

18. The method of claim 1, wherein the reservoir has a maximum cross-sectional area that is greater than a maximum cross-sectional area of the volume of the specimen tube.

19. The method of claim 1, wherein the cap is coupled to the specimen tube via a thread connection which secures the cap to an internal threading of the specimen tube.

20. The method of claim 1, wherein a portion of the reservoir extends into the volume of the specimen tube when the cap is secured to the specimen tube thereby enclosing the volume and reservoir to collectively from the specimen container therein.

21. The method of claim 1, wherein after centrifuging and before orienting the specimen container, the blood cells and the separator are disposed only in the reservoir, and a portion of the serum or plasma is disposed in the reservoir and a remaining portion of the serum or plasma is disposed in the volume of the specimen tube.

22. The method of claim 1, wherein after centrifuging and before orienting the specimen container, the blood cells, the separator, and the serum or plasma are disposed only in the reservoir.

23. A method of separating blood cells from a blood specimen with a specimen container, the specimen container including a specimen tube defining an inner volume, and a cap defining a reservoir, the method comprising:
disposing the blood specimen into the inner volume through an open end of the specimen tube;
securing the cap to the specimen tube, thereby enclosing the inner volume and the reservoir;
with a separator disposed within at least one of the inner volume or the reservoir, disposing the specimen container in a centrifuge, the centrifuge having an axis of centrifugation;
centrifuging the specimen container with the cap further away from the axis of centrifugation than a closed end of the specimen tube such that the blood cells of the blood specimen and the separator migrate into the reservoir and remain in the reservoir after the centrifuging; and
orienting the specimen container with the cap above the closed end of the specimen tube, the cap being at least partially removable from the specimen tube to expose the open end of the specimen tube such that the serum or plasma can be withdrawn through the open end of the specimen tube.

24. The method of claim 23, wherein the volume of the specimen tube is about 0.1 mL to about 2.0 mL, and the closed end of the specimen tube is round.

25. The method of claim 23, wherein prior to the centrifuging, the cap is secured to the specimen tube such that the cap is spaced apart from the closed end of the specimen tube.

26. The method of claim 23, wherein the separator includes at least one of a thixotropic gel, a mechanical separator, or a filter-based separator.

27. A method of separating blood cells from a blood specimen with a specimen container, the specimen container including a specimen tube defining an inner volume, and a cap defining a reservoir, the method comprising:
disposing the blood specimen into the inner volume through an open end of the specimen tube;
securing the cap to the specimen tube, thereby enclosing the inner volume and the reservoir;
disposing the specimen container in a centrifuge, the centrifuge having an axis of centrifugation;
centrifuging the specimen container with the cap further away from the axis of centrifugation than a closed end of the specimen tube such that the blood cells of the blood specimen migrate into the reservoir and remain in the reservoir after the centrifuging; and
orienting the specimen container with the cap above the closed end of the specimen tube, the cap being at least partially removable from the specimen tube to expose the open end of the specimen tube such that the serum or plasma can be withdrawn through the open end of the specimen tube, the reservoir in the cap having a volume (1) defined as the maximum amount of liquid that can be contained in the cap without contacting the specimen tube and (2) equal to or greater than a volume of the blood cells and other solids separated from the blood specimen.

28. The method of claim 27, wherein the centrifuging occurs without a separator disposed in the inner volume and without a separator disposed in the reservoir, and such that the centrifuging packs the blood cells in the reservoir such that the blood cells remain in the cap after the centrifuging and when the cap is at least partially removed from the specimen tube to expose the open end of the specimen tube.

29. The method of claim 27, wherein the reservoir has a maximum cross-sectional area that is greater than a maximum cross-sectional area of the volume of the specimen tube.

30. The method of claim 27, wherein a portion of the cap circumferentially surrounds a portion of the specimen tube when the cap is secured to the specimen tube.

* * * * *